United States Patent
Kerr

(10) Patent No.: US 9,585,640 B2
(45) Date of Patent: Mar. 7, 2017

(54) METHOD OF MAKING AN ELLIPTICAL SKIN PUNCH

(71) Applicant: James Henry Kerr, San Diego, CA (US)

(72) Inventor: James Henry Kerr, San Diego, CA (US)

( * ) Notice: Subject to any disclaimer, the term of this patent is extended or adjusted under 35 U.S.C. 154(b) by 244 days.

(21) Appl. No.: 14/278,345

(22) Filed: May 15, 2014

(65) Prior Publication Data

US 2014/0343455 A1    Nov. 20, 2014

Related U.S. Application Data

(60) Provisional application No. 61/823,115, filed on May 14, 2013.

(51) Int. Cl.
  *A61B 10/00* (2006.01)
  *A61B 10/02* (2006.01)
(52) U.S. Cl.
  CPC .. *A61B 10/0233* (2013.01); *A61B 2010/0208* (2013.01)

(58) Field of Classification Search
  CPC .................. A61B 10/0233; A61B 2010/0208
  USPC ................................................ 600/567–568
  See application file for complete search history.

(56) References Cited

U.S. PATENT DOCUMENTS

| | | | |
|---|---|---|---|
| 6,331,166 B1 * | 12/2001 | Burbank | A61B 90/17 600/567 |
| 2007/0232954 A1 * | 10/2007 | Harris | A61B 10/02 600/564 |
| 2014/0336530 A1 * | 11/2014 | Vetter | A61B 10/0266 600/567 |

* cited by examiner

*Primary Examiner* — Kristen Matter

(57) ABSTRACT

Attaching an elliptical excisional skin biopsy punch to an appropriately designed hand held electrically powered handle can quickly produce a sharply demarcated wound that is the same shape and size as the elliptical punch that was used. The biopsy specimen obtained in this manner can be obtained within 1-2 seconds and thus is a much faster method than the more laborious method of rocking the elliptical punch back and forth by hand. In addition, only slight pressure is required to complete the biopsy thus minimizing the crush effect on the biopsy specimen.

1 Claim, 4 Drawing Sheets

METHOD OF MAKING AN ELLIPTICAL SKIN PUNCH

RELATED APPLICATIONS

This application claims benefit of provisional patent application No. U.S. 61/823,115, filed on May 14, 2013.

FEDERALLY SPONSORED DEVELOPMENT

Not Applicable

BACKGROUND OF THE INVENTION

This invention involves a modified technique to produce a more efficient use of an approved medical device—the elliptical excisional skin biopsy punch. Commercially available elliptically shaped skin biopsy punches have been available for decades. However, due to the elliptical shape of the cutting blade of this type of punch, it cannot be rotated back and forth like a round punch to do a skin biopsy. Instead the manufacturer recommended technique advises the insertion of one of the angled ends of the elliptically shaped blade into the skin and then forcibly rocking the blade back and forth to cut through the skin. This technique requires heavy pressure and prolonged rocking back and forth to cut through the skin. Even so, this technique produces poor quality biopsy specimens without clean edges and with increasing crush effect with the smaller size punches. This technique also obviates the main advantages of an elliptically shaped excision which are to produce a wound that is easier to surgically close and to produce a more pleasing cosmetic scar than that produced by a round punch biopsy.

This invention describes a modified technique that makes the elliptical excisional biopsy punch fast and efficient in producing a sharply demarcated elliptically shaped wound by attaching the handle of the punch to a hand-held battery powered driver unit. This driver unit produces very rapid and short, back and forth oscillations of the attached elliptical punch blade in an almost vibratory motion which allows it to quickly slice completely through the involved skin in 1-2 seconds. Also, the resulting biopsy specimen has sharp edges with little crush effect and the resulting wound maintains the shape and size of any sized punch that is used.

Figure 1:
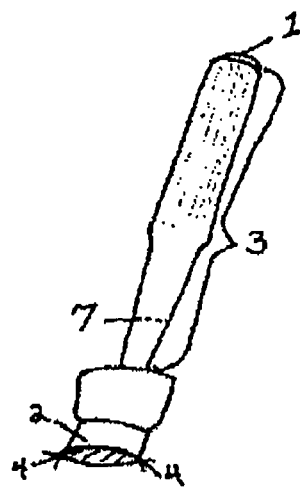
FIG. 1 displays an unmodified elliptical skin punch.
Figure 2:
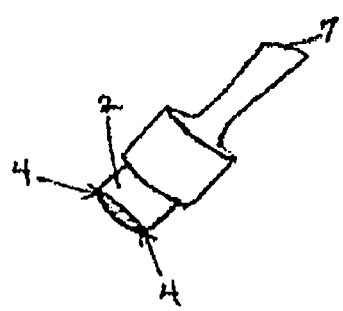
FIG. 2 displays the modified cutting portion of the elliptical excisional skin punch.
Figure 3:
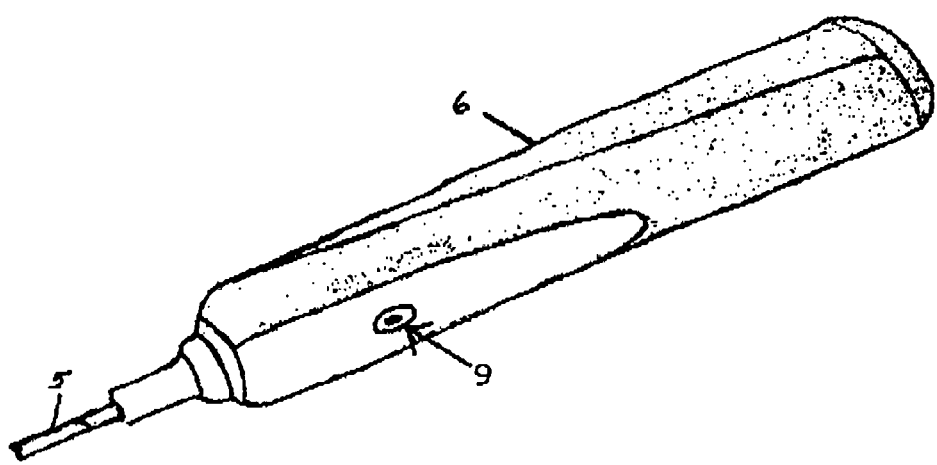
FIG. 3 displays the hand-held electrically powered driver unit.
Figure 4:
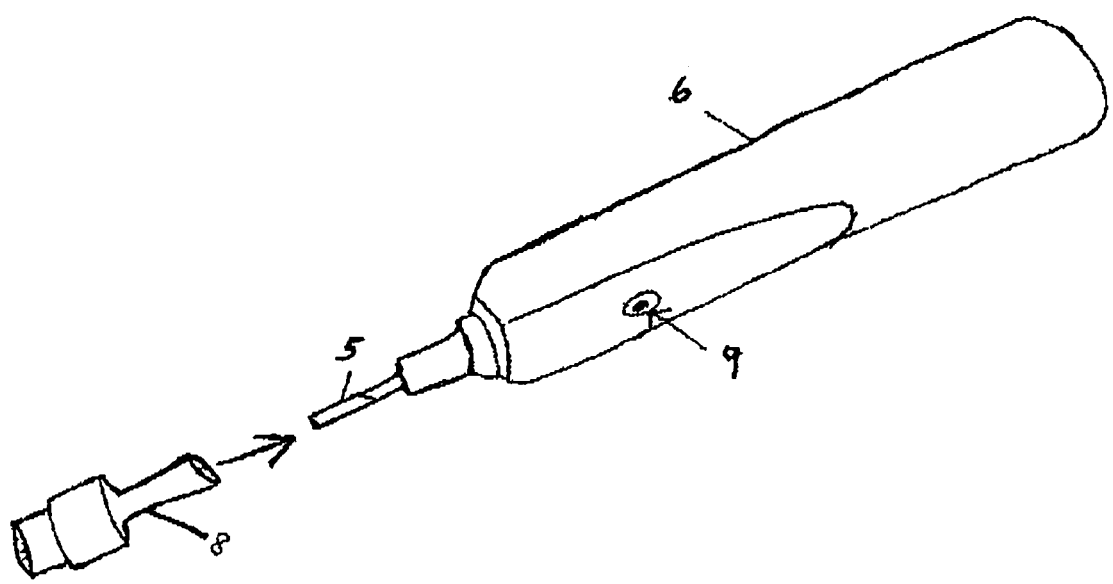
FIG. 4 displays the process of how the elliptical excisional skin punch is modified and attached to the hand-held driver unit.
Figure 5:
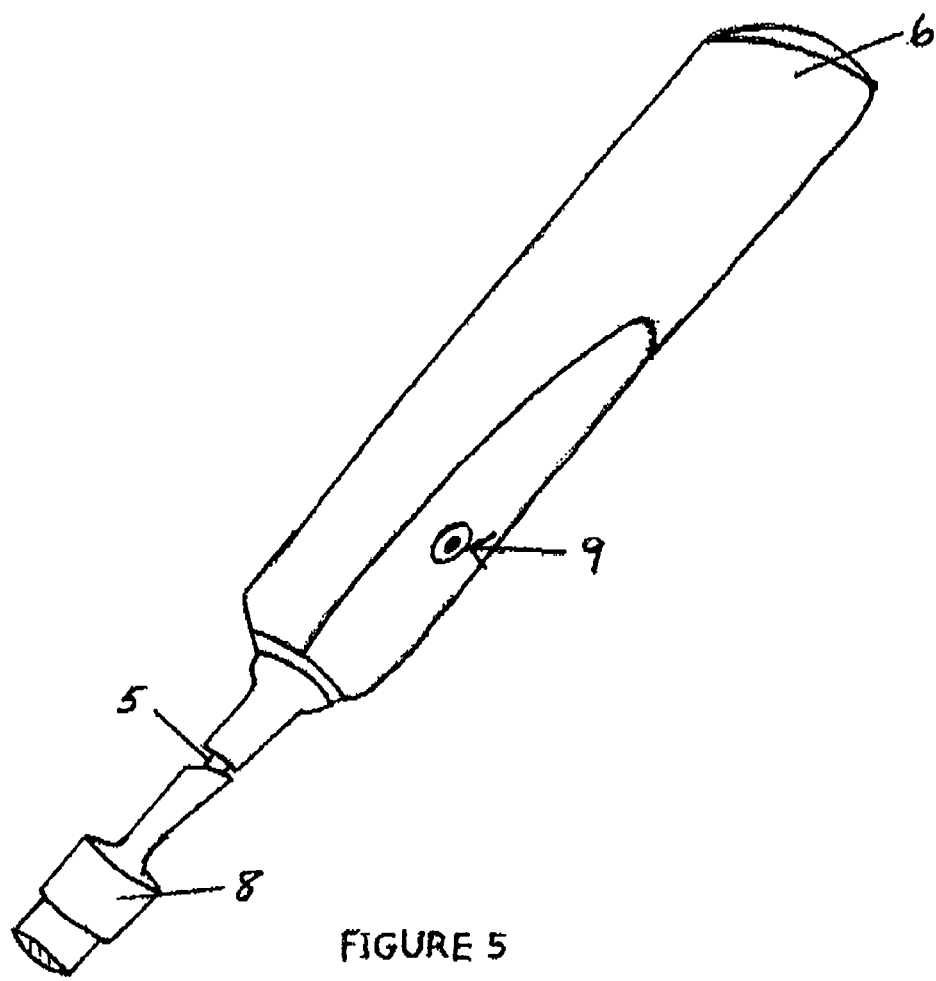
FIG. 5 displays the driver unit with the modified elliptical excisional skin punch attached.

Identifying part numbers (in parentheses) used in the application and in each Figure remain the same throughout.

DETAILED DESCRIPTION OF THE INVENTION

This invention involves a new technique to greatly improve the effectiveness and efficiency of a medically approved, existing surgical instrument, the disposable elliptical excislonal skin biopsy punch. To accomplish this, the tapered, hollow plastic handle (3) of the elliptical punch (1) is modified to fit onto the metal shaft (5) of a handheld, battery powered or rechargeable driver unit (6). At present the rechargeable Braun Professional Care or Oral B Professional toothbrush handle has the required vibratory motion to produce the desired effect on an attached modified elliptical punch. A very sharp, elliptically shaped, surgical steel blade (2) is embedded into the end of the plastic punch and Is made with 30 degree angles (4) at both ends of the elliptical blade. The use of this elliptically shaped blade produces a skin biopsy wound that is optimal for a sutured linear closure that produces a better cosmetic result than other available skin biopsy punches.

Since the hollow plastic handle of the punch is larger than the metal shaft of the available prototype handheld battery powered/rechargeable driver unit, the hollow handle is cut in two at the narrower part of the handle (7) at about 1.5 Inches above the cutting edge of the blade. This allows the narrow part of the hollow handle to be wedged onto the metal driver shaft. At that point, the modified hollow handle (8) can be wedged tightly enough onto the metal shaft to allow adequate transfer of the vibratory motion of the activated metal shaft to the attached elliptical blade. When the driver unit, a rechargeable Braun Professional Care or Oral B Professional (powered by Braun) toothbrush handle is activated with the power button (9), it produces the proper vibratory motion that is transferred via the attached handle to the elliptical punch blade. When the activated punch blade is then placed onto the skin in the desired location, it produces a clean, sharply demarcated biopsy using minimal pressure within 1-2 seconds. This technique produces excellent results with any available size elliptical punch.

The elliptical punch could also be attached to the driver without any modification if a larger sized shaft on the driver unit became available. Another future option might be an appropriately designed adapter that fits over the metal shaft of the driver and into the unmodified hollow shaft of the elliptical punch.

The invention claimed is:

1. A method for modifying an elliptical shaped surgical biopsy punch comprising:
    providing a skin excision device comprising a plastic, hollow handle and an elliptical shaped surgical steel blade with a cutting edge;
    cutting the handle of the skin excision device about 1.5 inches above the cutting edge of the blade; and
    tightly securing the cut handle of the skin excision device to a metal shaft of a hand-held electrically powered driver such that vibratory motion of the metal shaft is transferred to the blade when the driver is activated in order to produce a skin biopsy wound when the blade is placed onto the skin of a user.

* * * * *